(12) United States Patent
Pasupuleti et al.

(10) Patent No.: US 12,154,035 B2
(45) Date of Patent: *Nov. 26, 2024

(54) ANATOMICAL POSITION MONITORING FOR BODILY PRESSURE ULCERS

(71) Applicant: VENTECH SOLUTIONS, INC., Columbus, OH (US)

(72) Inventors: Ravi Kiran Pasupuleti, Triplicane Chennai (IN); Ravi Kunduru, Columbus, OH (US)

(73) Assignee: Ventech Solutions, Inc., Columbus, OH (US)

( * ) Notice: Subject to any disclaimer, the term of this patent is extended or adjusted under 35 U.S.C. 154(b) by 95 days.

This patent is subject to a terminal disclaimer.

(21) Appl. No.: 18/112,898

(22) Filed: Feb. 22, 2023

(65) Prior Publication Data
US 2023/0206078 A1    Jun. 29, 2023

Related U.S. Application Data

(63) Continuation of application No. 16/800,238, filed on Feb. 25, 2020, now Pat. No. 11,676,031.

(51) Int. Cl.
*G06N 3/04*  (2023.01)
*G06N 3/084*  (2023.01)
*G16H 40/67*  (2018.01)

(52) U.S. Cl.
CPC .............. *G06N 3/084* (2013.01); *G06N 3/04* (2013.01); *G16H 40/67* (2018.01)

(58) Field of Classification Search
CPC ..... A61B 5/447; A61B 5/0064; A61B 5/0531; A61B 5/7264; A61B 2560/0247;
(Continued)

(56) References Cited

U.S. PATENT DOCUMENTS 8,806,647 B1   8/2014 Daswani
10,009,666 B1  6/2018 van Scheltinga
(Continued)

OTHER PUBLICATIONS

"MID_Tracking_and_Identifying_People_with_Millimeter_Wave_Radar" by Zhao et al. (2019) (Year: 2019).*

*Primary Examiner* — Cindy Trandai
(74) *Attorney, Agent, or Firm* — Mahamedi IP Law LLP

(57) ABSTRACT

A method and system of training a machine learning neural network (MLNN) in monitoring anatomical positioning. The method comprises receiving, in a first input layer, from millimeter wave (mmWave) radar device, mmWave point cloud data representing spatial positions associated with a medical patient during successive changes in the spatial positions corresponding durations between changes, the mmWave data based upon detecting range and reflected wireless signal strength, receiving, in a second layer of the MLNN, attribute data for the corresponding durations, the f input layers interconnected with an output layer via an intermediate layer, the intermediate layer configured with an initial matrix of weights, training a MLNN classifier using classification that establishes correlation between the mmWave radar point cloud data, the attribute data and likelihood of formation of bodily pressure ulcers (BPUs) generated at the output layer, and producing a trained MLNN based on increasing the correlation.

20 Claims, 5 Drawing Sheets

(58) Field of Classification Search
CPC ... A61B 5/0507; A61B 5/1114; A61B 5/1126; A61B 5/441; A61B 2562/0247; A61B 5/026; G06N 3/084; G06N 3/04; G06N 3/08; G16H 40/67; G16H 30/40; G16H 40/40; G06T 7/0012; G06T 2207/20081; G06T 2207/20084
See application file for complete search history.

(56) References Cited

U.S. PATENT DOCUMENTS

| | | | |
|---|---|---|---|
| 11,043,219 B1 | 6/2021 | Walters | |
| 2007/0263907 A1* | 11/2007 | McMakin | G06V 40/25 382/107 |
| 2008/0079989 A1 | 4/2008 | Agnetta | |
| 2009/0210419 A1 | 8/2009 | Chignis | |
| 2010/0201378 A1 | 8/2010 | Costanzo | |
| 2011/0018657 A1 | 1/2011 | Cheng | |
| 2012/0319821 A1 | 12/2012 | Karttaavi | |
| 2013/0227695 A1 | 8/2013 | Shankar | |
| 2013/0232472 A1 | 9/2013 | Korner | |
| 2013/0290322 A1 | 10/2013 | Prosnitz | |
| 2014/0121527 A1 | 5/2014 | Adler, Jr. | |
| 2014/0221825 A1 | 8/2014 | Mahfouz | |
| 2015/0248536 A1 | 9/2015 | Tawil | |
| 2017/0224253 A1 | 8/2017 | Berlin | |
| 2017/0238867 A1 | 8/2017 | Javed | |
| 2018/0144465 A1 | 5/2018 | Hsieh | |
| 2018/0199996 A1 | 7/2018 | Hogan | |
| 2019/0104951 A1* | 4/2019 | Valys | G16H 50/20 |
| 2019/0104982 A1* | 4/2019 | Dunn | A61B 5/7264 |
| 2019/0180174 A1 | 6/2019 | Koswatta | |
| 2019/0342012 A1* | 11/2019 | Tonolini | G01S 1/74 |
| 2020/0113488 A1 | 4/2020 | Al-Ali | |
| 2020/0218974 A1* | 7/2020 | Cheng | G06N 3/044 |
| 2020/0250387 A1 | 8/2020 | Hiraoka | |
| 2021/0043205 A1 | 2/2021 | Lee | |
| 2021/0080563 A1* | 3/2021 | Meftah | A61B 90/98 |
| 2021/0192762 A1 | 6/2021 | Guan | |
| 2021/0225378 A1 | 7/2021 | Montemurro | |
| 2022/0139070 A1 | 5/2022 | Okamoto | |

* cited by examiner

300

| |
|---|
| Receiving, in a first input layer of the MLNN, from a millimeter wave (mmW) radar sensing device, mmW radar point cloud data representing a set of anatomical positions of the medical patient in association with a corresponding set of durations  310 |

↓

| |
|---|
| Receiving, in at least a second layer of the MLNN, attendant attribute data for the corresponding set of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device  320 |

↓

| |
|---|
| Training a MLNN classifier in accordance with a supervised classification that establishes a correlation between a likelihood of formation of BPUs as generated at the output layer with the mmW point cloud data and the attendant attribute data  330 |

↓

| |
|---|
| Adjusting the initial matrix of weights by backpropagation thereby to increase the correlation with the likelihood of formation of BPUs as generated at the output layer  340 |

300

Deploying the trained MLNN classifier upon receiving, in real time from an edge computing device associated with a subsequent medical patient, subsequent mmW point cloud data at the first input layer and circumstance attribute data received in the at least a second input layer.

510

Generating, at the output layer, a likelihood of formation of pressure ulcers for the subsequent medical patient

ANATOMICAL POSITION MONITORING FOR BODILY PRESSURE ULCERS

RELATED APPLICATION

This application is a Continuation of U.S. patent application Ser. No. 16/800,238 filed Feb. 25, 2020; the aforementioned priority application being hereby incorporated by reference in its entirety.

TECHNICAL FIELD

The disclosure herein relates to neural network systems for anatomical position monitoring.

BACKGROUND

Despite improvements in medical industry and healthcare, the incidence of bodily pressure ulcers remains a common concern for hospitalized patients. Bodily pressure ulcers, otherwise known as bedsores, prevails mostly in the patients who stay in hospital for long-term, assisted living at home, paralyzed patients and with other physical disorders in which patients are bedridden. Pressure ulcers manifest as skin lesions which adversely influence the patient's integrity of life and can become a significant source of morbidity and in some aspects, increased mortality. Managing and treating pressure ulcers are too costly. Though many devices have been designed with the aim of pressure ulcer prevention and cure but most of the existing technically complex devices have been exposed to be no more efficient and cost effective. Prevalence of these ulcers can be achieved by reducing pressures at bodily bony prominences while in supine and similar bodily orientations. In some cases, bedridden patients are often unaware of their limited body movements and repositioning that is critical for blood circulation and relieving of prolonged pressure on the body pressure points. In order to prevent or relieve the aforementioned effects, continuous variation and repositioning in patient's body postures, based on monitored status, is typically necessary.

BRIEF DESCRIPTION OF THE DRAWINGS

FIG. 3 illustrates a method of operation, in one example embodiment, of a system for training a machine learning neural network (MNLL) in anatomical position monitoring.

FIG. 5 illustrates a method of operation, in one example embodiment, of a privacy-centric edge computing system for deploying anatomical position monitoring related to bodily pressure ulcers.

DETAILED DESCRIPTION

Figure 1:
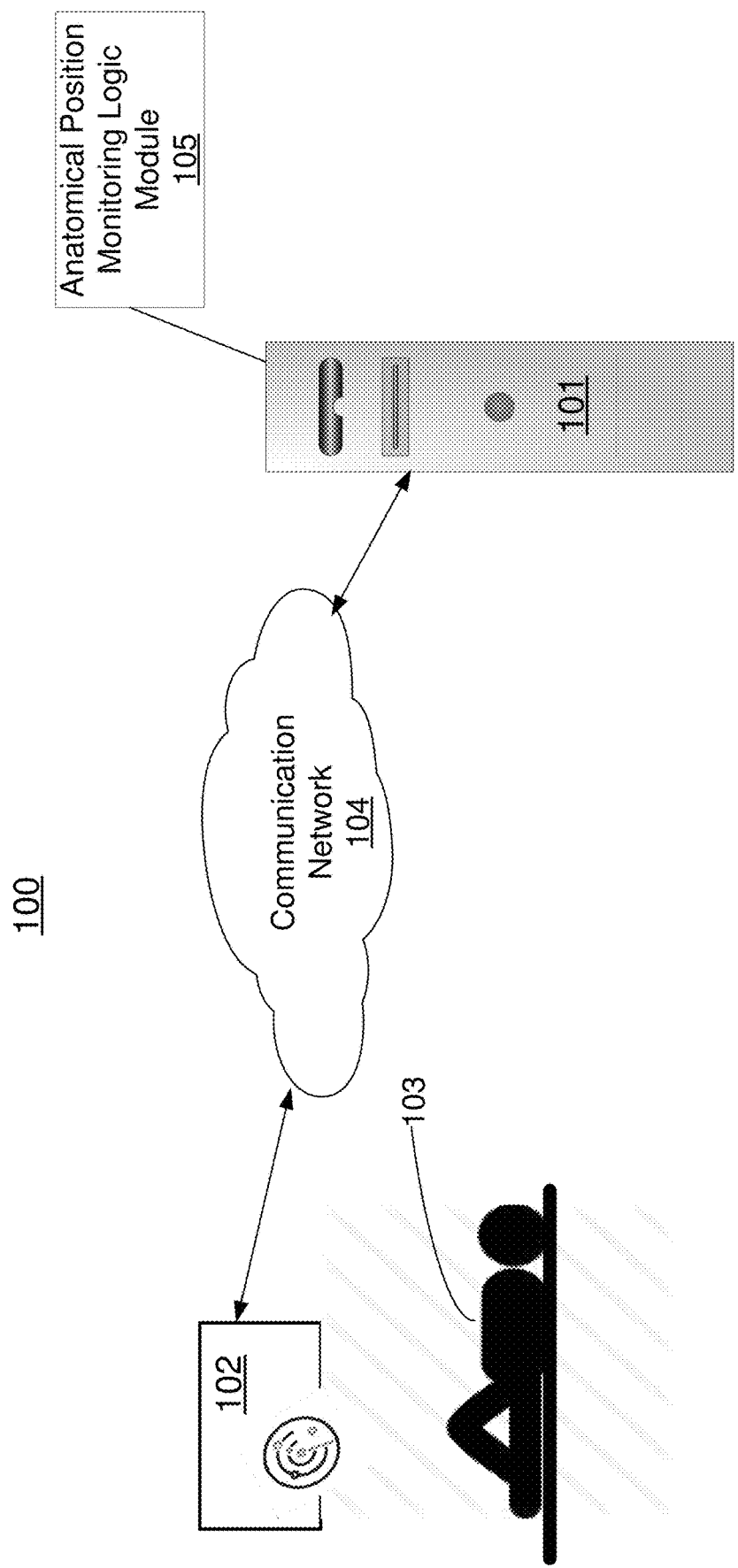
FIG. 1 illustrates, in an example embodiment, a system for training a machine learning neural network (MNLL) in anatomical position monitoring.

Methods and systems provided herein, among other advantages and benefits, to enable mmWave radar radio-frequency (RF) based sensing technologies to deliver automatic monitoring and support features for medical patients living independently in their homes, as well as people suffering from chronic diseases that require them to stay in care-homes or at hospitals. In particular, via supervised training of a neural network correlating anatomical features and positioning of a medical patent, based on mmWave radar sensing, with a likelihood of formation of bodily pressure ulcers (BPUs). Furthermore, the neural network as trained can be deployed in a privacy-centric system using an edge computing device in accordance with a medical patient's privacy related considerations and preferences.

Millimeter wave (mmWave) radar sensing technology as described and applied herein refers to detection of objects and providing information on range, velocity and angle of those objects. mmWave radar uses a contactless technology which operates in the spectrum between 30 GHz and 300 GHz, using small wavelengths that provide sub-mm range accuracy and is able to penetrate materials such as plastic, drywall, clothing, and is impervious to environmental conditions like rain, fog, dust and snow. As opposed to commercial radar techniques, the disclosure herein implements a high-resolution mmWave radar sensor to obtain a relatively richer radar point cloud representation for tracking and monitoring of a medical patient anatomical features, limbs and extremities. Advantageously, in embodiments implemented herein, 60-GHz mmWave sensors provide 4 GHz of UWB bandwidth, resulting in 16 times the available bandwidth than 24-GHz sensors for high-accuracy mmWave radar applications.

As referred to herein, a point cloud refers to a set of data points in space. As the output of 3D scanning processes, in this case a mmWave 3D scanning and sensing operations, point clouds are used to capture anatomical feature data of the medical patient. mm Wave radar is based on the principle of frequency modulated continuous wave (FMCW) radar, which has the ability to simultaneously measure the range and relative radial speed of a target point. A mmWave radar sensor is applied herein to produce point clouds, of varying density of data points in some embodiments, by making repeated measurements as the body of the medical patient moves, each time getting a slightly different point of view. It transmits an RF signal and records reflection from the target point that is collected in the point cloud, the point cloud data including the object's ID, range, angle, velocity and signal strength delivered, in one embodiment, over a computing and communication interface. The object ID may be a patient ID in some embodiments.

As described herein, the neural networks, in embodiments, refer to an artificial intelligence (AI) based neural network having interconnected nodes and assemblies of nodes representing layers of the neural network, including machine learning (ML) or deep learning (DL) models. In a particular embodiment, the ML or neural network model herein may be implemented as a convolution neural network (CNN).

In accordance with a first example embodiment, provided is a method of training a machine learning neural network (MLNN) in monitoring anatomical positioning causing bodily pressure ulcers (BPUs) of a medical patient. The method is performed in one or more processors and comprises receiving, in a first input layer of the MLNN, from a millimeter wave (mmWave) radar sensing device, mmWave radar point cloud data representing a set of anatomical positions of the medical patient in association with a corresponding set of durations; receiving, in at least a second layer of the MLNN, attendant attribute data for the corresponding set of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device; training a MLNN classifier in accordance with a supervised classification that establishes a correlation between a likelihood of formation of BPUs as generated at the output layer with the mmWave point cloud data and the attendant attribute data; and adjusting the initial matrix of weights by backpropagation thereby to increase the correlation with the likelihood of formation of BPUs as generated at the output layer.

In embodiments, the backpropagation comprises recursively adjusting the initial matrix of weights in diminishment of an error matrix calculated at the output layer thereby to increase the correlation with the likelihood of BPUs.

In some aspects, the mmWave radar point cloud data includes bodily pressure points data relative to a patient support platform between changes in successive ones of the set of anatomical positions in accordance with the corresponding set of durations.

In embodiments, the attendant attribute data comprises at least one of patient specific data and environmental attribute data pertaining to the corresponding set of durations.

In embodiments, the patient specific data includes one or more of a patient age, weight, blood pressure, height, sex, pulse rate, and any physical profile parameter inherent to an individual patient.

In an embodiment, the environmental attribute data comprises one or more of a temperature measurement, a humidity measurement, and a category of physical infrastructure in which the medical patient is located.

In embodiments, the mmWave radar sensing device comprises a 60 GHz mmWave radar sensing device.

In embodiments, the method further comprises deploying the trained MLNN classifier upon establishing that the correlation with the likelihood of formation of BPUs exceeds a 90 percent threshold value.

In an embodiment, the method further comprises deploying the trained MLNN classifier upon receiving, in real time from an edge computing device, subsequent mmWave point cloud data at the first input layer and attendant attribute data received in the at least a second input layer. The edge computing device, which may be a desktop or laptop computing device, or an Internet of Things (IoT) device, provides a privacy-centric deployment system associated with the subsequent medical patient.

In the deployment, one aspect provides for tracking multiple patients based on a respective patient ID assigned in conjunction with their respective mmWave radar signature (point cloud and density). This way a single mmWave radar unit can monitor multiple patients in a controlled setting, such as in a ward or ICU hospital or medical clinic setting.

In one aspect, the method further comprises generating, at the output layer, a likelihood of formation of pressure ulcers for the subsequent medical patient.

In accordance with a second example embodiment, a non-transitory medium storing instructions executable in a processor of a server computing device is provided. The instructions, when executed in one or more processors, cause operations comprising receiving, in a first input layer of a MLNN, from a millimeter wave (mmWave) radar sensing device, mmWave radar point cloud data representing a set of anatomical positions of the medical patient in association with a corresponding set of durations; receiving, in at least a second layer of the MLNN, attendant attribute data for the corresponding set of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device; training a MLNN classifier in accordance with a supervised classification that establishes a correlation between a likelihood of formation of BPUs as generated at the output layer with the mmWave point cloud data and the attendant attribute data; and adjusting the initial matrix of weights by backpropagation thereby to increase the correlation with the likelihood of formation of BPUs as generated at the output layer.

In accordance with a third example embodiment, a computing system implement AI or a machine learning neural network (MLNN) in monitoring anatomical positioning causing bodily pressure ulcers (BPUs) of a medical patient. The computing system, which in embodiments can an edge computing device or a server computing device, includes one or processors and a memory storing instructions, which, when executed in the one or more processors causing operations comprising receiving, in a first input layer of the MLNN, from a millimeter wave (mmWave) radar sensing device, mmWave radar point cloud data representing a set of anatomical positions of the medical patient in association with a corresponding set of durations; receiving, in at least a second layer of the MLNN, attendant attribute data for the corresponding set of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device; training a MLNN classifier in accordance with a supervised classification that establishes a correlation between a likelihood of formation of BPUs as generated at the output layer with the mmWave point cloud data and the attendant attribute data; and adjusting the initial matrix of weights by backpropagation thereby to increase the correlation with the likelihood of formation of BPUs as generated at the output layer.

One or more embodiments described herein provide that methods, techniques, and actions performed by a computing device are performed programmatically, or as a computer-implemented method. Programmatically, as used herein, means through the use of code or computer-executable instructions. These instructions can be stored in one or more memory resources of the computing device.

Furthermore, one or more embodiments described herein may be implemented through the use of logic instructions that are executable by one or more processors of a computing device, including a server computing device. These instructions may be carried on a computer-readable medium. In particular, machines shown with embodiments herein include processor(s) and various forms of memory for storing data and instructions. Examples of computer-readable mediums and computer storage mediums include portable memory storage units, and flash memory. A server computing device as described herein utilizes processors, memory, and logic instructions stored on computer-readable medium. Embodiments described herein may be implemented in the form of computer processor-executable logic instructions or programs stored on computer memory mediums.

System Description

FIG. 1 illustrates, in an example embodiment, a system 100 for training a machine learning neural network (MNLL) in anatomical position monitoring. Server computing system or server device 101, also referred to herein as server 101, includes anatomical position monitoring logic module 105 embodied according to computer processor-executable instructions stored within a non-transitory memory. Server 101 is in communication via communication network 104 with mmWave sensing and communication device 102, sensing and monitoring anatomical dispositions of medical patient 103 upon a support platform.

Figure 2:
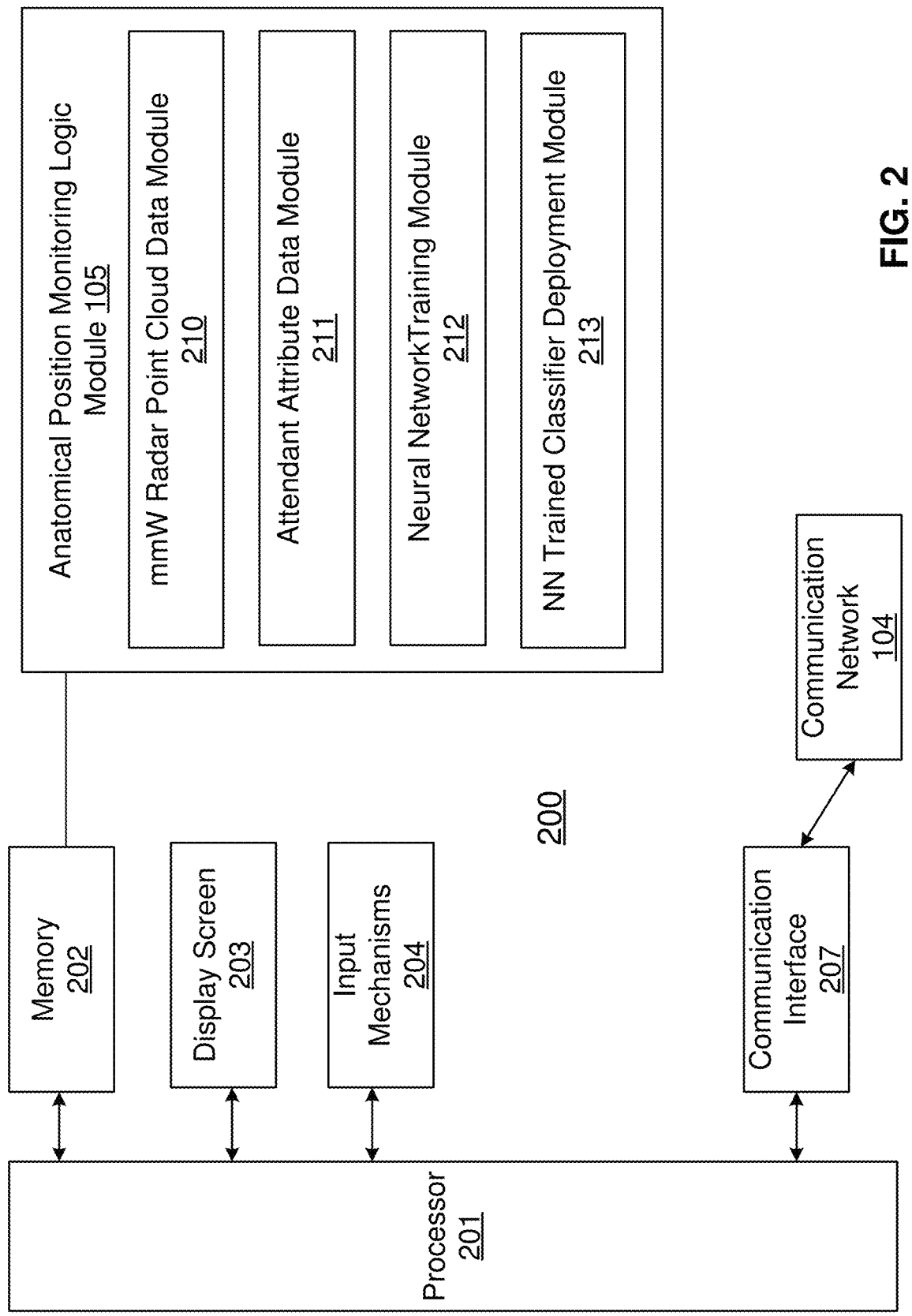
FIG. 2 illustrates, in one example embodiment, an architecture of a system for training a machine learning neural network (MNLL) in anatomical position monitoring.

FIG. 2 illustrates, in one example embodiment, an architecture of a system 200 for training a machine learning neural network (MNLL) in anatomical position monitoring. Server computing system or device 101, also referred to herein as server 101, may include processor 201, memory 202, display screen 203, input mechanisms 204 such as a keyboard or software-implemented touchscreen input functionality, and communication interface 207 for communicating via communication network 104. Memory 202 may comprise any type of non-transitory system memory, storing instructions that are executable in processor 201, including such as a static random access memory (SRAM), dynamic random access memory (DRAM), synchronous DRAM (SDRAM), read-only memory (ROM), or a combination thereof.

Anatomical position monitoring logic module 105 includes processor-executable instructions stored in memory 202 of server 101, the instructions being executable in processor 201. Anatomical position monitoring logic module 105 may comprise portions or sub-modules including mmWave radar point cloud data module 210, attendant attribute data module 211, neural network training module 212, and neural network trained classifier deployment module 213.

Processor 201 uses executable instructions of mmWave radar point cloud data module 210 to receive, in a first input layer of the MLNN, from a millimeter wave (mmWave) radar sensing device, mmWave radar point cloud data representing a set of anatomical positions of the medical patient in association with a corresponding set of durations.

Processor 201 uses executable instructions stored in attendant attribute data module 211 to receive, in at least a second layer of the MLNN, attendant attribute data for the corresponding set of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device.

Processor 201 uses executable instructions stored in neural network training module 212 to train a MLNN classifier in accordance with a supervised classification that establishes a correlation between a likelihood of formation of BPUs as generated at the output layer with the mmWave point cloud data and the attendant attribute data.

In the particular embodiment of a convolution neural network model, the convolution operation typically embodies two parts of inputs: (i) input feature map data, and (ii) a weight (also referred to as output filter, or kernel). Given the input channel data with W (Width)×H (Height)×IC data cube and R×S×IC filter, the output of direct convolution may be formulated as:

$$y_{w,h} = \sum_{r=0}^{R-1}\sum_{s=0}^{S-1}\sum_{c=0}^{C-1} x_{(w+r),(h+s),c} * W_{r,s,c}$$

where:
X=input data/input feature/input feature map
w=width of the input or output data
h=height of the input or output data
R=weight size (width)
S=weight size (height)
C=number of input channel
Y=output data/output feature/output feature map
W=filter/kernel/weight For each input channel, the filter, or weight, are convoluted with data and generates output data. The same location of data of all the input channels are summed together and generate 1 output data channel.

The weight or filter is applied to correlate an anatomical position of a body member or extremity with a likelihood of BPUs being formed thereon, based on an input data stream of mmWave radar point cloud data representing anatomical positions of the medical patient's body relative to a support platform, such as a hospital bed.

Each output channel of the convolution model is represented by an output filter or weight used to detect one particular feature or pattern of the input feature data stream. Convolution neural networks constituted of interconnected node assemblies can include many output filters or weights for each layer of the convolution model corresponding to respective features or patterns in the data stream of input features.

In embodiments, training the neural network classifier comprises recursively adjusting the initial matrix of weights by backpropogation in diminishment of a number of the false positive vulnerability defects generated at the output layer in accordance with the supervised classification.

In some embodiments, the backpropagation comprises a backward propagation of errors in accordance with an error matrix as computed at the output layer, the errors being distributed backwards throughout the weights of the at least one neural network intermediate layer.

In some embodiments, diminishment of the number of false positive vulnerability defects proceeds, based on the recursively adjusting, in accordance with diminishment of an error matrix computed at the output layer of the neural network classifier.

Processor 201 uses executable instructions stored in neural network trained classifier deployment module 213 to adjust the initial matrix of weights by backpropagation thereby to increase the correlation with the likelihood of formation of BPUs as generated at the output layer.

Methodology

FIG. 3 illustrates a method of operation, in one example embodiment, of a system for training a machine learning neural network (MNLL) in anatomical position monitoring, method 300 being performed by one or more processors 201 of server computing device 101. In describing and performing the embodiments of FIG. 3, the examples of FIG. 1 and FIG. 2 are incorporated for purposes of illustrating suitable components or elements for performing a step or sub-step being described.

Examples of method steps described herein relate to the use of server 101 for implementing the techniques described. According to one embodiment, the techniques are performed by Anatomical Position Monitoring Logic Module 105 of server 101 in response to the processor 201 executing one or more sequences of software logic instructions that constitute Anatomical Position Monitoring Logic Module 105.

In embodiments, anatomical position monitoring logic module 105 includes the one or more sequences of instructions within sub-modules including mmWave radar point cloud data module 210, attendant attribute data module 211 and Neural network training module 212. Such instructions may be read into memory 202 from machine-readable medium, such as memory storage devices. In executing the sequences of instructions contained in mmWave radar point cloud data module 210, attendant attribute data module 211 and Neural network training module 212 of Anatomical Position Monitoring Logic Module 105 in memory 202, processor 201 performs the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, processor 201 executes instructions of mmWave radar point cloud data module 210 to receive, in a first input layer of the MLNN, from a millimeter wave (mmWave) radar sensing device, mmWave radar point cloud data representing a set of anatomical positions of the medical patient in association with a corresponding set of durations.

At step 320, processor 201 of server computing device 101 executes instructions included in attendant attribute data module 211 to receive, in at least a second layer of the MLNN, attendant attribute data for the corresponding set of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device.

At step 330, processor 201 executes instructions included in Neural network training module 212, to train a MLNN classifier in accordance with a supervised classification that establishes a correlation between a likelihood of formation of BPUs as generated at the output layer with the mmWave point cloud data and the attendant attribute data.

At step 340, processor 210 executes instructions included in neural network trained classifier deployment module 213 to adjust the initial matrix of weights by backpropagation thereby to increase the correlation with the likelihood of formation of BPUs as generated at the output layer.

In embodiments, the backpropagation comprises recursively adjusting the initial matrix of weights in diminishment of an error matrix calculated at the output layer thereby to increase the correlation with the likelihood of BPUs.

In some aspects, the mmWave radar point cloud data includes bodily pressure points data relative to a patient support platform between changes in successive ones of the set of anatomical positions associated with corresponding durations of time between the changes. Based on the sensed positions such as the patient disposed in a supine position on the platform, actual anatomical points of rest or contact with the platform can be sensed according to the mmWave point cloud sensing device 102, providing an inference of such as pressure points upon which BPUs can develop or form.

In embodiments, the attendant attribute data comprises at least one of patient specific data and environmental attribute data pertaining to the corresponding set of durations.

In embodiments, the patient specific data includes one or more of a patient age, weight, blood pressure, height, sex, pulse rate, and any physical profile parameter inherent to an individual patient.

In an embodiment, the environmental attribute data comprises one or more of a temperature measurement, a humidity measurement, and a category of physical infrastructure in which the medical patient is located.

In some embodiments, the mmWave radar sensing device comprises a 60 GHz mmWave radar sensing device.

The neural networks of embodiments herein refer to an artificial intelligence (AI) based neural network, including machine learning (ML) or deep learning (DL) models, constituted of interconnected nodes, and assemblies of nodes. In a particular embodiment, the ML or neural network model herein may be implemented as a convolution neural network (CNN).

Figure 4:
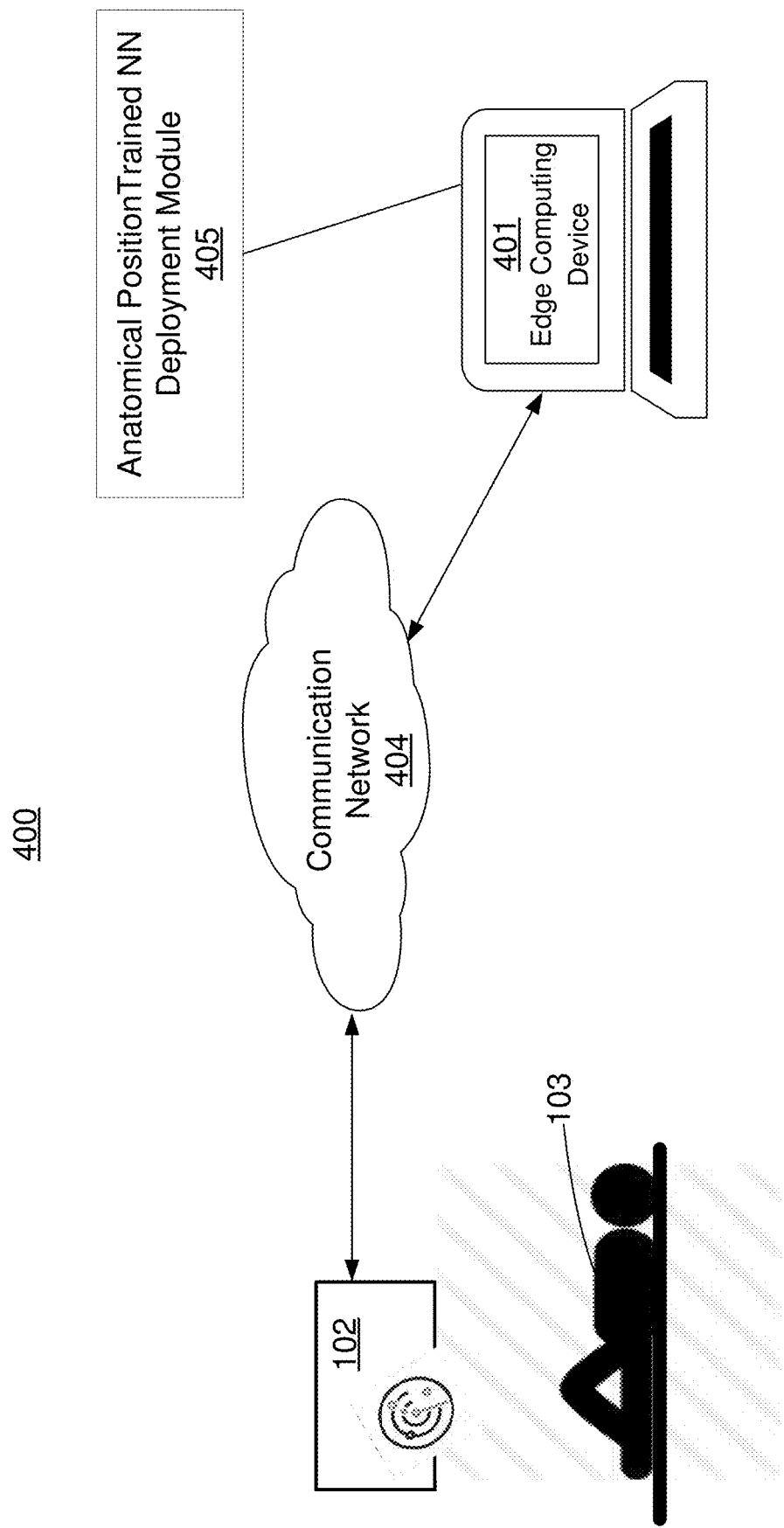
FIG. 4 illustrates a privacy-centric edge computing system for deploying anatomical position monitoring related to bodily pressure ulcers.

FIG. 4 illustrates a privacy-centric edge computing system 400 for deploying anatomical position monitoring related to bodily pressure ulcers using a trained classifier, optionally performed in conjunction with the disclosures of FIG. 3 herein. In the privacy-centric embodiment, system 400 is based on deployment of anatomical position trained neural network deployment module 405, in accordance with the supervised training as described with regard to FIGS. 1-3 herein. System 400 may be located in a single bounded infrastructure, such as a patient's room or home. In this embodiment, the patient is monitored and advised within the local infrastructure, via local communication network 404 in an embodiment as depicted, ensuring privacy at the patient's option. No information from mmWave radar based monitoring need be uploaded or shared to a cloud, in accordance with the patient's privacy preferences. Edge computing device 401, which may be a laptop or desktop computer, or an Internet of Things (IoT) computing device, provides computing resources for deploying a trained anatomical position monitoring system as described herein with regard to FIGS. 1-3. The patient may be advised using media speakers operable in conjunction with edge computing device 401, as to when to modify detected anatomical positions in order to avoid or ameliorate a likelihood of developing BPUs.

FIG. 5 illustrates a method of operation, in one example embodiment, of a privacy-centric edge computing system for deploying anatomical position monitoring related to bodily pressure ulcers using the trained classifier in conjunction with the disclosures of FIGS. 1-4. In some aspects, such deploying proceeds once the trained classifier, based on the supervised training as described herein with regard to FIG. 3, for example, produces a sufficiently high correlation in predicting formation of BPUs with high enough accuracy of prediction. In one embodiment, the deploying proceeds when the trained classifier attains at least a threshold limit of 90 percent likelihood of predicting formation of BPUs.

At step 510, deploying the trained MLNN classifier upon receiving, in real time from an edge computing device, subsequent mmWave point cloud data at the first input layer and attendant attribute data received in the at least a second input layer. The edge computing device, which may be a desktop or laptop computing device, or an Internet of Things (IoT) device, provides a privacy-centric deployment system associated with the subsequent medical patient.

At step 520, generating, at the output layer, a likelihood of formation of pressure ulcers for the subsequent medical patient. Based upon that likelihood, a patient may be advised or instructed via interactive media or audio speakers to change positioning at regular or more frequent intervals in order to avoid or minimize, potential formation of BPUs.

In the deployment, one aspect provides for tracking multiple patients based on a respective patient ID assigned in conjunction with their respective mmWave radar signature (point cloud and density). This way a single mmWave radar unit can monitor multiple patients in a controlled setting, such as in a ward or ICU hospital or medical clinic setting.

It is contemplated that embodiments described herein extend to individual elements and concepts described herein, as well as for embodiments to include combinations of elements recited anywhere in this application. Although embodiments are described in detail herein with reference to the accompanying drawings, it is to be understood that the invention is not limited to only such example embodiments. As such, many modifications and variations will be apparent to practitioners skilled in the art. Accordingly, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mention of the particular feature. Thus, the absence of describing combinations should not preclude the inventors from claiming rights to such combinations.

What is claimed is:

1. A method, performed in a computing device, of training a machine learning neural network (MLNN) in monitoring anatomical positioning of a medical patient, the method performed in one or more processors and comprising:
   receiving, in a first input layer of the MLNN, from a millimeter wave (mmWave) radar sensing device, mmWave radar point cloud data representing a plurality of spatial positions of an anatomical target associated with the medical patient during changes in successive ones of the plurality of spatial positions in association with a corresponding plurality of durations between the changes, the mmWave radar point data based upon detecting at least a range and a reflected wireless signal strength associated with the anatomical target;
   receiving, in at least a second layer of the MLNN, attendant attribute data for the corresponding plurality of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device;
   training a MLNN classifier in accordance with a classification that establishes a correlation between the mmWave radar point cloud data, the attendant attribute data and a likelihood of formation of bodily pressure ulcers (BPUs) as generated at the output layer; and
   producing a trained MLNN based on increasing the correlation.

2. The method of claim 1 further comprising increasing the correlation based at least in part on adjusting the initial matrix of weights by backpropagation.

3. The method of claim 2 wherein the backpropagation comprises recursively adjusting the initial matrix of weights in diminishment of an error matrix calculated at the output layer thereby increasing the correlation with the likelihood of BPUs.

4. The method of claim 1 wherein the mmWave radar point cloud data includes bodily pressure points data relative to a patient support platform between changes in successive ones of the plurality of spatial positions in accordance with the corresponding plurality of durations.

5. The method of claim 1 wherein the attendant attribute data comprises at least one of patient specific data and environmental attribute data pertaining to the corresponding plurality of durations.

6. The method of claim 5 wherein the patient specific data includes at least one of a patient age, weight, blood pressure, height, sex, and pulse rate.

7. The method of claim 5 wherein the environmental attribute data comprises at least one of a temperature measurement, a humidity measurement, and a category of physical infrastructure in which the medical patient is located.

8. The method of claim 1 wherein the mmWave radar sensing device comprises a 60 GHz mmWave radar sensing device.

9. The method of claim 1 wherein the medical patient is a first medical patient and further comprising:
   deploying the trained MLNN in prediction of formation of BPUs upon establishing that, in accordance with the correlation, the likelihood of formation of BPUs exceeds a predetermined threshold value; and
   generating, at the output layer, a likelihood of formation of pressure ulcers for a second medical patient.

10. The method of claim 9 further comprising deploying the trained MLNN classifier upon receiving, in real time from an edge computing device, subsequent mmWave point cloud data at the first input layer and attendant attribute data received in the at least a second input layer, the edge computing device providing a privacy-centric deployment system associated with the subsequent medical patient.

11. A computing system comprising:
   one or more processors;
   a memory storing a set of instructions, the instructions when executed in the one or more processors causing operations comprising:
   receiving, in a first input layer of a machine learning neural network (MLNN), from a millimeter wave (mmWave) radar sensing device, mmWave radar point cloud data representing a plurality of spatial positions of an anatomical target associated with a medical patient during changes in successive ones of the plurality of spatial positions in association with a corresponding plurality of durations between the changes, the mmWave radar point data based upon detecting at least a range and a reflected wireless signal strength associated with the anatomical target;
   receiving, in at least a second layer of the MLNN, attendant attribute data for the corresponding plurality of durations, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in the memory;
   training a MLNN classifier in accordance with a classification that establishes a correlation between the mmWave radar point cloud data, the attendant attribute data and a likelihood of formation of bodily pressure ulcers (BPUs) as generated at the output layer; and
   producing a trained MLNN based on increasing the correlation.

12. The computing system of claim 11 further comprising instructions executable in the one or more processors, which, when executed cause operations including increasing the correlation based at least in part on adjusting the initial matrix of weights by backpropagation.

13. The computing system of claim 12 wherein the backpropagation comprises recursively adjusting the initial matrix of weights in diminishment of an error matrix calculated at the output layer thereby increasing the correlation with the likelihood of BPUs.

14. The computing system of claim 11 wherein the mmWave radar point cloud data includes bodily pressure points data relative to a patient support platform between changes in successive ones of the plurality of spatial positions in accordance with the corresponding plurality of durations.

15. The computing system of claim 11 wherein the attendant attribute data comprises at least one of patient specific data and environmental attribute data pertaining to the corresponding plurality of durations.

16. The computing system of claim 15 wherein the patient specific data includes at least one of a patient age, weight, blood pressure, height, sex, and pulse rate.

17. The computing system of claim 15 wherein the environmental attribute data comprises at least one of a temperature measurement, a humidity measurement, and a category of physical infrastructure in which the medical patient is located.

18. The computing system of claim 11 wherein the mmWave radar sensing device comprises a 60 GHz mmWave radar sensing device.

19. The computing system of claim 11 wherein the medical patient is a first medical patient and further comprising instructions executable in the one or more processors, which, when executed cause operations including:
 deploying the trained MLNN in prediction of formation of BPUs upon establishing that, in accordance with the correlation, the likelihood of formation of BPUs exceeds a predetermined threshold value; and
 generating, at the output layer, a likelihood of formation of pressure ulcers for a second medical patient.

20. The computing system of claim 19 further comprising instructions executable in the one or more processors, which, when executed cause operations including deploying the trained MLNN classifier upon receiving, in real time from an edge computing device, subsequent mmWave point cloud data at the first input layer and attendant attribute data received in the at least a second input layer, the edge computing device providing a privacy-centric deployment system associated with the subsequent medical patient.

* * * * *